US00PP34884P2

(12) United States Plant Patent
Jones

(10) Patent No.: US PP34,884 P2
(45) Date of Patent: Jan. 3, 2023

(54) ***LEUCOPHYLLUM* PLANT NAMED 'MSWNHELEI'**

(50) Latin Name: ***Leucophyllum frutescens* X *Leucophyllum pringlei***
Varietal Denomination: MSWNHelei

(71) Applicant: Camelot Nurseries Inc., Glendale, AZ (US)

(72) Inventor: Kelly Jones, Glendale, AZ (US)

(73) Assignee: CAMELOT NURSERIES INC., Glendale, AZ (US)

( * ) Notice: Subject to any disclaimer, the term of this patent is extended or adjusted under 35 U.S.C. 154(b) by 15 days.

(21) Appl. No.: 17/537,416

(22) Filed: Nov. 29, 2021

(51) Int. Cl.
*A01H 5/00* (2018.01)
*A01H 6/00* (2018.01)
*A01H 5/02* (2018.01)

(52) U.S. Cl.
USPC ..... Plt./226
CPC ..... *A01H 6/00* (2018.05); *A01H 5/02* (2013.01)

(58) Field of Classification Search
USPC ..... Plt./226
See application file for complete search history.

*Primary Examiner* — Karen M Redden
(74) *Attorney, Agent, or Firm* — C. Anne Whealy

(57) ABSTRACT

A new and distinct cultivar of *Leucophyllum* plant named 'MSWNHelei', characterized by its relatively compact, outwardly spreading and low-growing and mounded plant habit; moderately vigorous growth habit; freely branching habit; dense and bushy appearance; relatively narrow, light green-colored leaves; freely flowering habit; relatively large purple-colored flowers; and good garden performance.

2 Drawing Sheets

Figure 1:
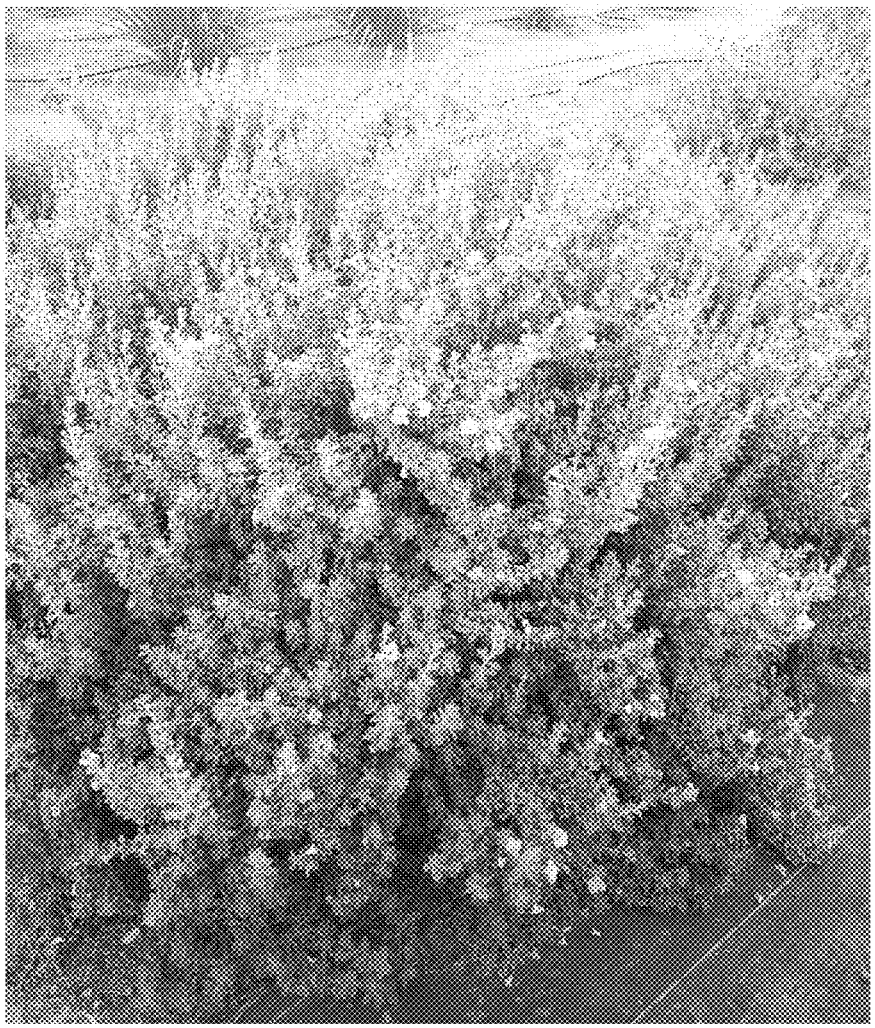

Botanical designation: *Leucophyllum frutescens* X *Leucophyllum pringlei.*
Cultivar denomination: 'MSWNHelei'.

STATEMENT REGARDING PRIOR DISCLOSURES BY INVENTOR/APPLICANT & ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or the Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Leucophyllum* plant, botanically known as *Leucophyllum frutescens* X *Leucophyllum pringlei* and hereinafter referred to by the name 'MSWNHelei'.

The new *Leucophyllum* plant is a product of a planned breeding program conducted by the Inventor in Glendale, Ariz. The objective of the breeding program is to create new relatively compact, dense and freely flowering *Leucophyllum* plants with attractive leaf and flower coloration.

The new *Leucophyllum* plant originated from a cross-pollination conducted by the Inventor in July, 2017 in Glendale, Ariz. of *Leucophyllum fructescens* 'Convent', not patented, as the female, or seed, parent with an unnamed selection of *Leucophyllum pringlei* as the male, or pollen, parent. The new *Leucophyllum* plant was discovered and selected by the Inventor as a single flowering plant from within the progeny of the stated cross-pollination in a controlled environment in Glendale, Ariz. on Feb. 28, 2018.

Asexual reproduction of the new *Leucophyllum* plant by terminal vegetative cuttings in a controlled environment in Glendale, Ariz. since August, 2018, has shown that the unique features of this new *Leucophyllum* plant are stable and reproduced true to type in successive generations.

SUMMARY OF THE INVENTION

Plants of the new *Leucophyllum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MSWNHelei'. These characteristics in combination distinguish 'MSWNHelei' as a new and distinct *Leucophyllum* plant:

1. Relatively compact, outwardly spreading and low-growing and mounded plant habit.
2. Moderately vigorous growth habit.
3. Freely branching habit; dense and bushy appearance.
4. Relatively narrow, light green-colored leaves.
5. Freely flowering habit.
6. Relatively large purple-colored flowers.
7. Good garden performance.

Plants of the new *Leucophyllum* differ primarily from plants of the female parent, 'Convent' in the following characteristics:

1. Plants of the new *Leucophyllum* are more compact than plants of 'Convent'.

2. Plants of the new *Leucophyllum* are more low-growing and mounding than and not as upright as plants of 'Convent'.
3. Leaves of plants of the new *Leucophyllum* are narrower than leaves of plants of 'Convent'.
4. Flowers of plants of the new *Leucophyllum* are purple in color whereas flowers of plants of 'Convent' are magenta in color.

Plants of the new *Leucophyllum* differ primarily from plants of the male parent selection in the following characteristics:

1. Leaves of plants of the new *Leucophyllum* are narrower and lighter green in color than leaves of plants of the male parent selection.
2. Flowers of plants of the new *Leucophyllum* are lighter purple in color than flowers of plants of the male parent.
3. Plants of the new *Leucophyllum* flower from late spring into autumn in Arizona whereas plants of the male parent selection flower from autumn until winter in Arizona.
4. Plants of the new *Leucophyllum* are more tolerant to overhead irrigation than plants of the male parent selection.

Plants of the new *Leucophyllum* can be compared to plants of *Leucophyllum frutescens* 'Heavenly Cloud', not patented. In side-by-side comparisons, plants of the new *Leucophyllum* differ primarily from plants of 'Heavenly Cloud' in the following characteristics:

1. Plants of the new *Leucophyllum* are much more compact than plants of 'Heavenly Cloud'.
2. Plants of the new *Leucophyllum* are more low-growing and mounding than and not as upright as plants of 'Heavenly Cloud'.
3. Leaves of plants of the new *Leucophyllum* are narrower and lighter green in color than leaves of plants of 'Heavenly Cloud'.
4. Flowers of plants of the new *Leucophyllum* are lighter purple in color than flowers of plants of 'Heavenly Cloud'.

BRIEF DESCRIPTION OF THE PHOTOGRAPHS

The accompanying colored photographs illustrate the overall appearance of the new *Leucophyllum* plant showing the colors as true as it is reasonably possible to obtain in colored reproductions of this type. Colors in the photographs may differ slightly from the color values cited in the detailed botanical description which accurately describe the colors of the new *Leucophyllum* plant.

The photograph on the first sheet (FIG. 1) is a side perspective view of a typical flowering plant of 'MSWNHelei' grown in an outdoor nursery.

Figure 2:
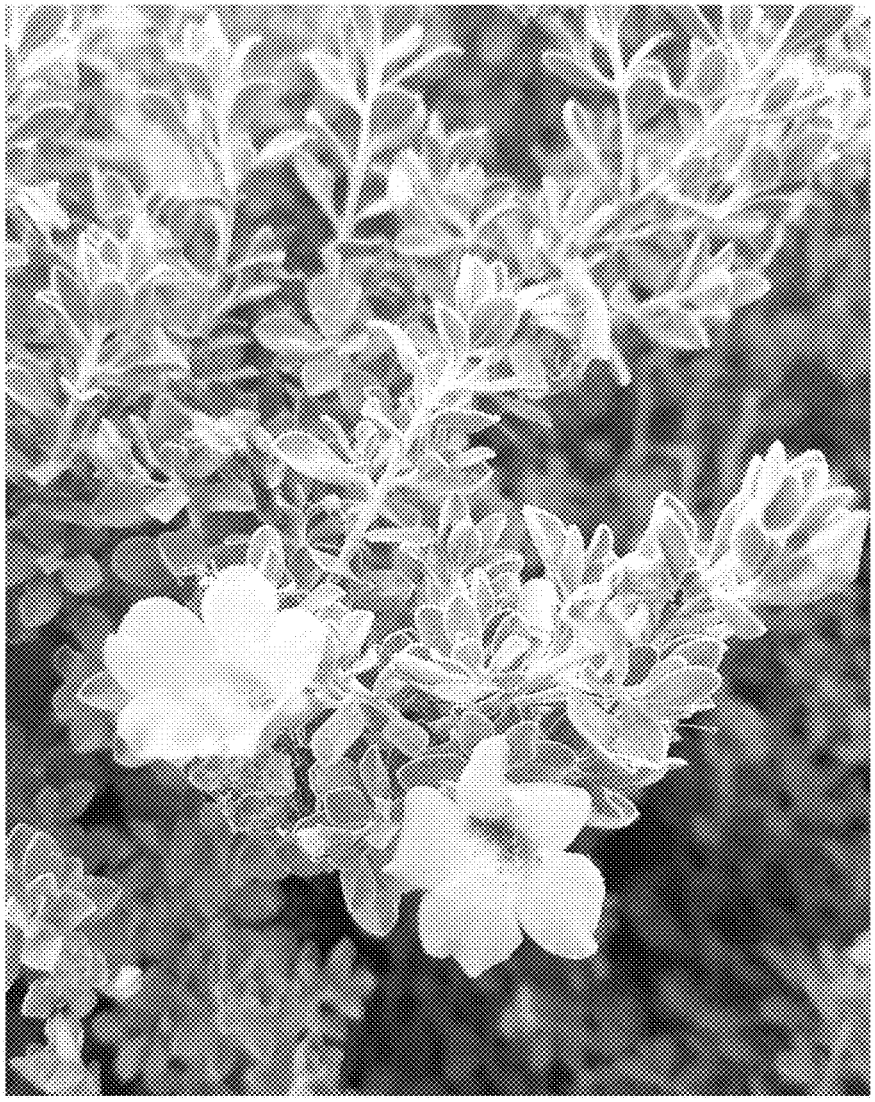

The photograph on the second sheet (FIG. 2) is a close-up view of a typical flowering plant of 'MSWNHelei'.

DETAILED BOTANICAL DESCRIPTION

The aforementioned photographs and following observations and measurements describe plants grown year-round in outdoor nurseries in Glendale, Ariz. and Fort Worth, Tex. and under cultural practices typical of commercial *Leucophyllum* production. Plants were four years old when the photographs were taken and three years old when the description was taken. In the following description, color references are made to The Royal Horticultural Society Colour Chart, 2015 Edition, except where general terms of ordinary dictionary significance are used.

Botanical classification: *Leucophyllum frutescens* X *Leucophyllum pringlei* 'MSWNHelei'.

Parentage:

*Female, or seed, parent.*—*Leucophyllum fructescens* 'Convent', not patented.

*Male, or pollen, parent.*—Unnamed selection of *Leucophyllum pringlei*, not patented.

Propagation:

*Type.*—By terminal vegetative cuttings.

*Time to initiate roots, summer.*—About 15 days at soil temperatures about 27° C.

*Time to initiate roots, winter.*—About 30 days at soil temperatures about 22° C.

*Time to produce a rooted young plant, summer.*—About 75 days at soil temperatures about 27° C.

*Time to produce a rooted young plant, winter.*—About 120 days at soil temperatures about 22° C.

*Root description.*—Medium in thickness, fibrous; typically white to light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Perennial shrub; relatively compact; outwardly spreading to low-growing and mounded plant habit; moderately vigorous growth habit and moderate growth rate; freely branching habit with lateral branches potentially developing at every node; dense and bushy appearance.

*Plant height.*—About 48 cm.

*Plant diameter.*—About 65 cm.

Lateral branch description:

*Length.*—About 57 cm.

*Diameter.*—About 3 mm.

*Internode length.*—About 1.5 cm.

*Strength.*—Strong; flexible when developing.

*Aspect.*—Primary stems, mostly upright to eventually trailing; lateral branches about 45° to 80° from primary stem axis.

*Texture and luster.*—Densely pubescent, lanate; matte; older stems, woody.

*Color, developing.*—Close to 143A; pubescence, close to 192A.

*Color, developed.*—Close to 143A variably tinged with close to 199A; pubescence, close to 192A and 193A; when woody, close to 199A and N199A.

Leaf description:

*Arrangement.*—Alternate, simple.

*Length.*—About 1.9 cm.

*Width.*—About 1.25 cm.

*Shape.*—Obovate.

*Apex.*—Obtuse with short cuspidate apex.

*Base.*—Cuneate to attenuate.

*Margin.*—Entire, not undulate.

*Texture and luster, upper and lower surfaces.*—Densely and finely pubescent, lanate; matte.

*Venation pattern.*—Pinnate.

*Color.*—Developing leaves, upper surface: Close to 138A. Developing leaves, lower surface: Close to 144A. Fully expanded leaves, upper surface: Close to 138A; venation, close to 138A. Fully expanded leaves, lower surface: Close to 146A; venation, close to 146B to 146C.

*Petioles*.—Length: About 1.5 mm. Diameter: About 1 mm. Strength: Strong, flexible. Texture and luster: Pubescent, lanate; matte. Color, upper and lower surfaces: Close to 138A.

Flower description:

*Flower arrangement and habit*.—Campanulate single flowers with five fused petals; flowers axillary; flowers face mostly outwardly; freely flowering habit with single flowers potentially developing at every axil during the flowering season.

*Fragrance*.—Faint; sweet and pleasant.

*Natural flowering season*.—Plants flower continuously from the late spring into autumn in Arizona and Texas.

*Flower longevity*.—Flowers last about two to three days on the plant; flowers not persistent.

*Flower size*.—About 2 cm by 2.1 cm.

*Flower depth*.—About 2.3 cm.

*Flower throat diameter*.—About 7 mm by 9 mm.

*Flower tube length*.—About 1.4 cm.

*Flower tube diameter, proximally*.—About 3 mm.

*Flower buds*.—Length: About 5 mm. Diameter: About 2.5 mm. Shape: Oblong. Texture and luster: Sepals, densely pubescent and matte. Color: Sepals, close to 144A.

*Petals*.—Arrangement: Five fused petals in a single whorl; lower 61% of the petals are fused, upper 39% of the petals are free; petal lobes reflexing with development. Petal lobe length: About 7.5 mm. Petal lobe width: About 7.5 mm. Petal lobe shape: Rounded with broadly obtuse apex. Petal lobe margin: Entire; slightly undulate. Petal lobe texture and luster, upper surface: Smooth, glabrous; somewhat velvety; matte. Petal lobe texture and luster, lower surface: Smooth, glabrous; slightly glossy. Throat, texture and luster: Upper surface of throat, smooth, glabrous and slightly glossy; lower surface of throat, densely pubescent and matte. Tube, texture and luster: Smooth, glabrous; slightly glossy. Color, petal lobes: When opening, upper and lower surfaces: Close to N82B. Fully opened, upper and lower surfaces: Close to N82B; venation, close to N82B; color becoming closer to N82C with subsequent development. Color, throat: Upper surface of throat, close to N82B to N82C; lower surface of throat, close to NN155D with spots, close to 163A to 163B; venation, similar to lamina colors. Color, tube: Upper surface of tube, close to N82B to N82C; lower surface of tube, close to NN155D with spots, close to 163A to 163B; venation, similar to lamina colors.

*Sepals*.—Arrangement: Tubular calyx with five sepals in a single whorl fused at the base. Calyx length: About 7.5 mm. Calyx diameter: About 3 mm. Sepal length: About 7.5 mm. Sepal width: About 1 mm. Shape: Linear. Apex: Acute. Margin: Entire. Texture and luster, upper surface: Smooth, glabrous with pubescence along the margins; slightly glossy. Texture and luster, lower surface: Densely pubescent; matte. Color, upper and lower surfaces: Close to 144A.

*Peduncles*.—Length: About 6 mm. Diameter: About 1 mm. Angle: About 45° from stem axis. Strength: Strong, flexible. Texture and luster: Densely pubescent; matte. Color: Close to 144A.

*Reproductive organs*.—Stamens: Quantity: Four per flower. Filament length: About 6 mm. Filament color: Close to NN155D. Anther size: About 2 mm by 1 mm. Anther shape: Bi-lobed, oblong. Anther color: Close to 158B. Pollen amount: None observed. Pistils: Quantity: One per flower. Pistil length: About 1.4 cm. Style length: About 8 mm. Style color: Close to NN155D. Stigma diameter: About 1 mm. Stigma shape: Semi-circular. Stigma color: Close to N77A. Ovary color: Close to 144B.

*Seeds and fruits*.—To date, seed and fruit development have not been observed on plants of the new *Leucophyllum*.

Pathogen resistance: To date, plants of the new *Leucophyllum* have not been observed to be resistant to pathogens common to *Leucanthemum* plants.

Garden performance: Plants of the new *Leucophyllum* have been observed to have good garden performance and to tolerate full sun condition, partial shade conditions, rain, wind, arid conditions and temperatures ranging from −12.2° C. to 47.8° C.

It is claimed:

1. A new and distinct *Leucophyllum* plant named 'MSWNHelei' as illustrated and described.

* * * * *